(12) United States Patent
Maschino et al.

(10) Patent No.: US 11,986,378 B2
(45) Date of Patent: May 21, 2024

(54) FLUID DISTRIBUTION MATERIAL FOR ABSORBENT ARTICLES

(71) Applicant: FITESA FILM PRODUCTS LLC, Simpsonville, SC (US)

(72) Inventors: Andrew D. Maschino, Paris, IL (US); Phillip A. Mellor, Simpsonville, SC (US); Jesse B. Schalburg, Simpsonville, SC (US)

(73) Assignee: FITESA FILM PRODUCTS LLC, Simpsonville, SC (US)

( * ) Notice: Subject to any disclaimer, the term of this patent is extended or adjusted under 35 U.S.C. 154(b) by 591 days.

(21) Appl. No.: 17/096,335

(22) Filed: Nov. 12, 2020

(65) Prior Publication Data
US 2021/0145657 A1 May 20, 2021

Related U.S. Application Data

(60) Provisional application No. 62/976,919, filed on Feb. 14, 2020, provisional application No. 62/935,480, filed on Nov. 14, 2019.

(51) Int. Cl.
*A61F 13/512* (2006.01)
*A61F 13/15* (2006.01)
(Continued)

(52) U.S. Cl.
CPC .... *A61F 13/5126* (2013.01); *A61F 13/15577* (2013.01); *A61F 13/5116* (2013.01);
(Continued)

(58) Field of Classification Search
CPC ............ A61F 13/5116; A61F 13/53713; A61F 13/53747; A61F 13/5126; A61F 2013/51165
See application file for complete search history.

(56) References Cited

U.S. PATENT DOCUMENTS 7,198,836 B2   4/2007 Thomas
2001/0047159 A1*  11/2001 Mizutani .......... A61F 13/47263
604/385.01
(Continued)

FOREIGN PATENT DOCUMENTS

CN    1213288 A    4/1999
CN    1705464 A    12/2005
(Continued)

OTHER PUBLICATIONS

Chinese Office Action dated Aug. 19, 2022, for Chinese Patent Application No. 202080086717.6.
(Continued)

*Primary Examiner* — Susan S Su
(74) *Attorney, Agent, or Firm* — KARCESKI IP LAW, PLLC

(57) ABSTRACT

A fluid distribution material for an absorbent article includes a formed film that includes a first side and a second side opposite the first side. The first side includes a plurality of elongated ridges extending from a first land area, a plurality of valleys defined by adjacent elongated ridges and the first land area, and a plurality of primary apertures located at bottoms of the valleys. The second side includes a plurality of apertured protuberances extending from a second land area. Each of the protuberances includes a continuous sidewall extending from the second land area to a distal end that includes a secondary aperture substantially aligned with a primary aperture. The formed film has a thickness greater than about 0.9 mm under a pressure of 0.071 psi, and a thickness greater than about 0.3 mm under a pressure of 0.6 psi.

12 Claims, 12 Drawing Sheets

(51) Int. Cl.
    *A61F 13/511*    (2006.01)
    *A61F 13/514*    (2006.01)
    *A61F 13/515*    (2006.01)
    *A61F 13/53*     (2006.01)
    *A61F 13/537*    (2006.01)

(52) U.S. Cl.
    CPC .......... *A61F 13/514* (2013.01); *A61F 13/515* (2013.01); *A61F 13/53* (2013.01); *A61F 13/53713* (2013.01); *A61F 13/53747* (2013.01); *A61F 2013/15926* (2013.01); *A61F 2013/51165* (2013.01)

(56) References Cited

U.S. PATENT DOCUMENTS

| | | | | |
|---|---|---|---|---|
| 2003/0093048 | A1* | 5/2003 | McBride | B32B 3/266 604/374 |
| 2004/0161586 | A1 | 8/2004 | Cree et al. | |
| 2005/0228353 | A1* | 10/2005 | Thomas | B29C 59/06 604/383 |
| 2005/0234417 | A1 | 10/2005 | Yoshimasa et al. | |
| 2005/0256475 | A1* | 11/2005 | Komatsu | A61F 13/5123 604/378 |
| 2012/0310197 | A1 | 12/2012 | Thomas | |

FOREIGN PATENT DOCUMENTS

| | | | | |
|---|---|---|---|---|
| CN | 203970682 U | 12/2014 | | |
| CN | 209361113 U | 9/2019 | | |
| JP | H07501244 A | 2/1995 | | |
| JP | 2005296480 A | 10/2005 | | |
| JP | 2006511367 A | 4/2006 | | |
| JP | 2007167212 A | * | 7/2007 | ............. A61F 13/15 |
| JP | 2007167212 A | | 7/2007 | |
| JP | 2009215667 A | * | 9/2009 | |
| JP | 2012120584 A | | 6/2012 | |

OTHER PUBLICATIONS

International Preliminary Report on Patentability dated May 27, 2022, for International Patent Application No. PCT/2022/060192.
Chinese Office Action dated Jan. 10, 2023, for Chinese Patent Application No. 202080086717.6.
Indian Office Action dated Sep. 15, 2022, for Indian Patent Application No. 202217027847.
International Search Report and Written Opinion dated Mar. 11, 2021, for International Patent Application No. PCT/US2020/060192.
Chinese Office Action dated Apr. 20, 2023, for Chinese Patent Application No. 202080086717.6.
Japanese Office Action dated Apr. 19, 2023, for Japanese Patent Application No. 2022-527184.
Japanese Office Action dated Oct. 31, 2023, for Japanese Patent Application No. 2022-527184.
Korean Office Action dated Nov. 9, 2023, for Korean Patent Application No. 10-2022-7019419.

* cited by examiner

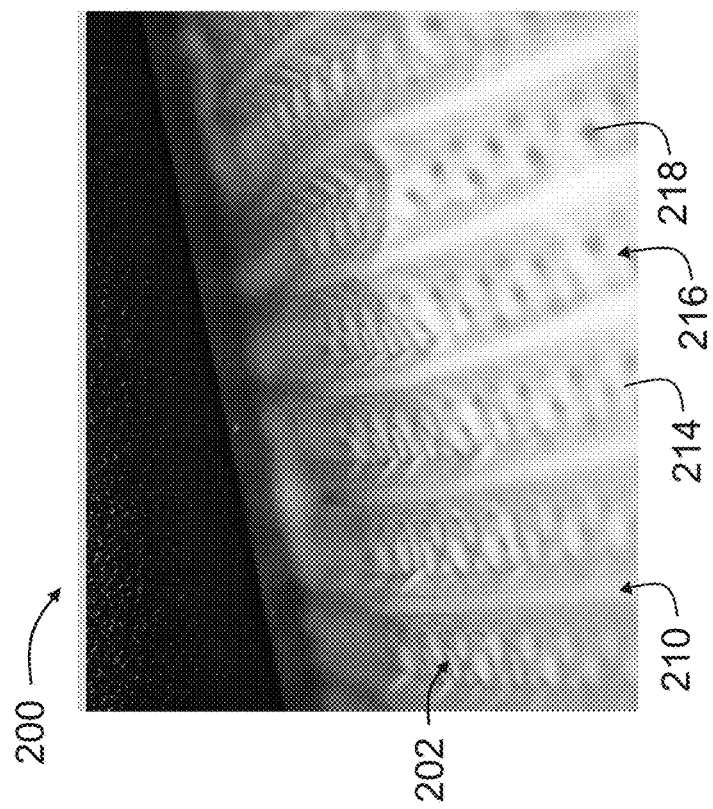
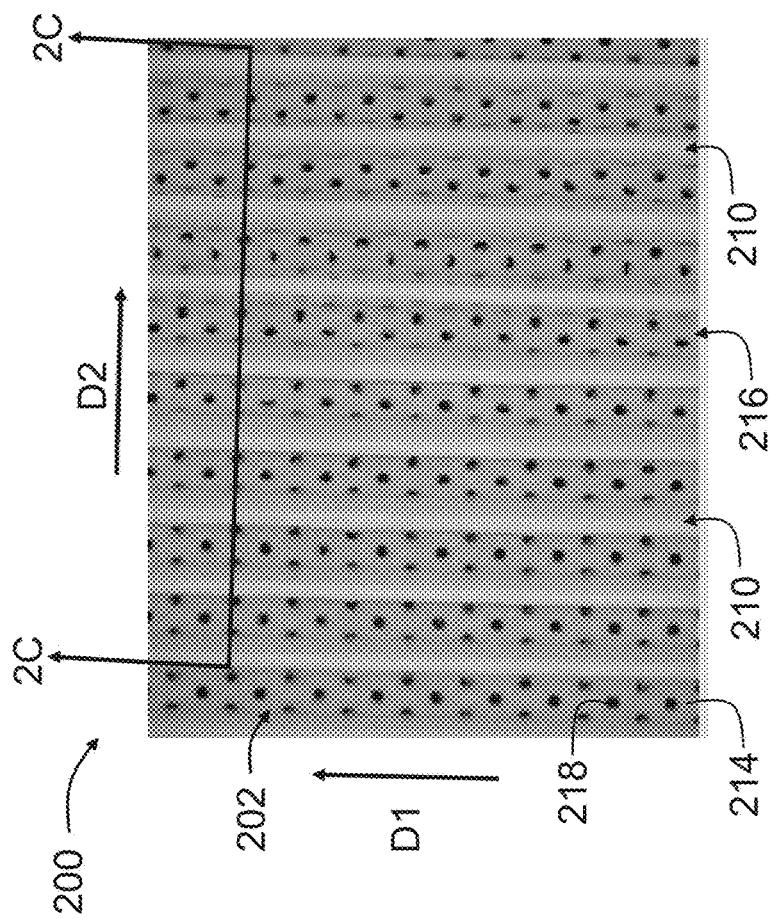
FIG. 2B
FIG. 2A

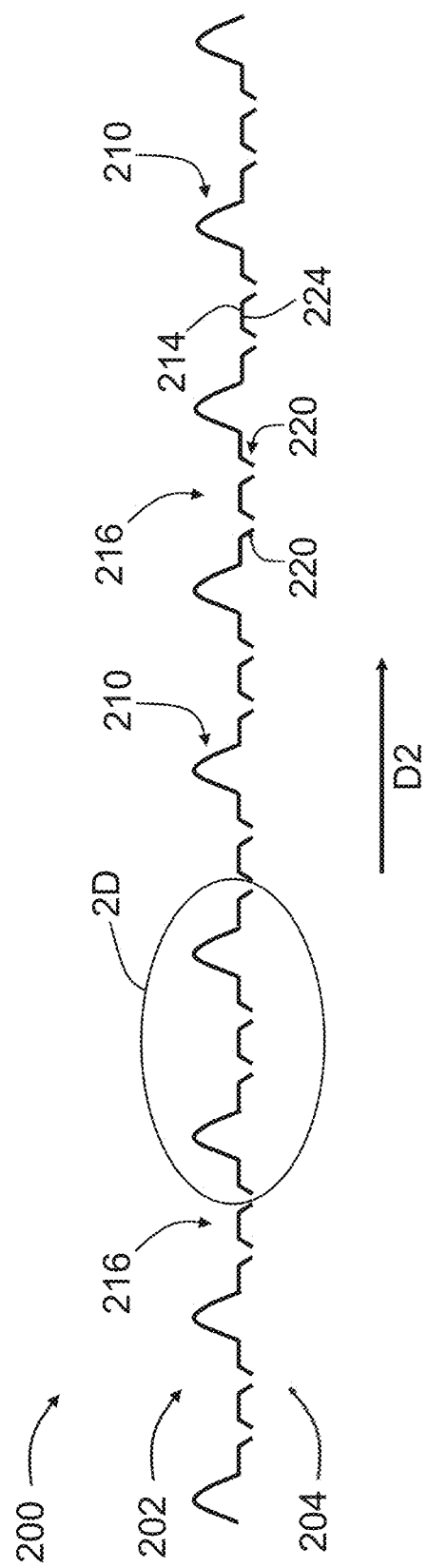

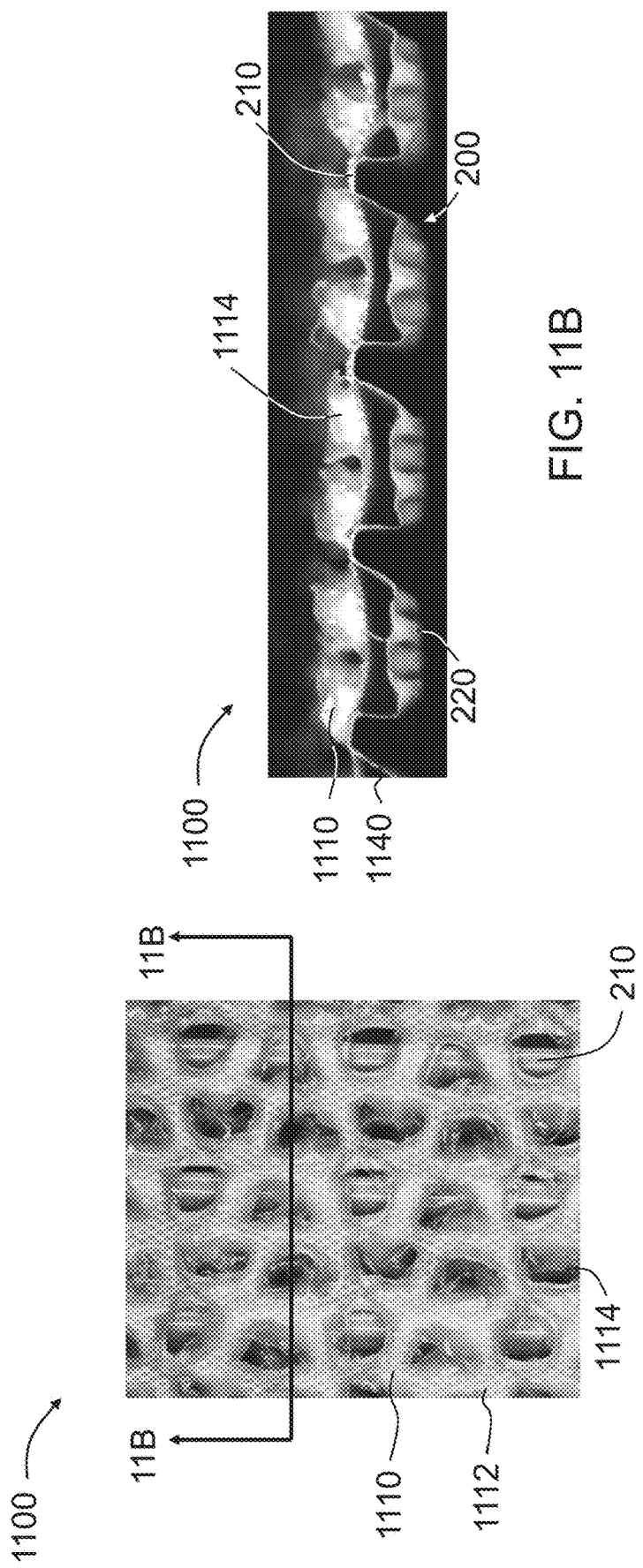

FLUID DISTRIBUTION MATERIAL FOR ABSORBENT ARTICLES

CROSS-REFERENCE TO RELATED APPLICATIONS

This application claims the benefit of priority from U.S. Provisional Patent Application Ser. No. 62/935,480, filed Nov. 14, 2019, and U.S. Provisional Patent Application Ser. No. 62/976,919, filed Feb. 14, 2020, the contents of both of which are hereby incorporated by reference in their entireties.

FIELD

The present invention is directed to a fluid distribution material that may be used in absorbent articles, as well as absorbent articles that include the fluid distribution material.

BACKGROUND

A variety of well-known absorbent articles are configured to absorb body fluids. Examples of such absorbent articles include, but are not limited to, feminine hygiene products, such as sanitary napkins, baby diapers, adult incontinence products, and bandages. A typical absorbent article is generally constructed with a fluid permeable user-facing topsheet, which may be a three dimensional apertured polymer film or a nonwoven web or a film/nonwoven laminate, an absorbent core and a fluid impermeable garment or outwardly-facing backsheet, which may be a solid polymer film, for example.

A potential problem associated with absorbent articles may be the perceived lack of dryness of the user-facing topsheet of the absorbent article. Generally, the drier the skin feels that is contacting topsheet, the more comfortable the absorbent article. In many instances, surface dryness of the topsheet may be correlated to fluid strikethrough efficiency. If the layer(s) beneath the topsheet are inefficient in fully pulling the fluid out of the topsheet, residual wetness can remain. Moreover, wetness may reoccur and contribute to residual wetness if the fluid is allowed to move from the layer(s) beneath the topsheet and back through the topsheet when the absorbent article is subjected to pressure, which is a typical condition when the article is being worn by a user.

One or more additional layers may be added to the absorbent article in between the topsheet and absorbent core to improve fluid acquisition out of the topsheet and/or fluid distribution across the absorbent core, so that the fluid may be pulled through and out of the topsheet and into the absorbent core more quickly and/or more completely, thus preventing the fluid from moving back through the topsheet. Because the absorbent core is generally rectangular in shape, it is desirable to move the fluid preferentially across the longer dimension rather that the shorter dimension. Such preferential movement may also reduce or prevent leakage out the side of the absorbent article, which is desirable.

SUMMARY

According to an aspect of the invention, there is provided a formed film for use as a fluid distribution material in an absorbent article that includes a topsheet, a backsheet, an absorbent core between the topsheet and backsheet. The formed film includes a first side that includes a plurality of elongated ridges extending from a first land area of the first side and oriented in a first direction, a plurality of valleys defined by adjacent elongated ridges and the first land area and oriented in the first direction, and a plurality of primary apertures located at bottoms of the valleys. The formed film includes a second side opposite the first side. The second side includes a plurality of apertured protuberances. Each of the apertured protuberances includes a continuous sidewall extending from a second land area of the second side to a distal end that includes a secondary aperture. Each secondary aperture is substantially aligned with a primary aperture. The formed film has a thickness greater than about 0.9 mm under a pressure of 0.071 psi, and a thickness greater than about 0.3 mm under a pressure of 0.6 psi.

In an embodiment, the first side is configured to face the topsheet and the second side is configured to face the absorbent core.

In an embodiment, the formed film has a basis weight between about 14 gsm and about 40 gsm.

In an embodiment, the plurality of apertured protuberances are arranged in a pattern having about 5 to about 45 apertured protuberances per linear inch in at least one direction.

According to an aspect of the invention, there is provided an absorbent article that includes a topsheet configured to contact skin of a user of the absorbent article, a backsheet configured to contact a garment of the user of the absorbent article, an absorbent core in between the topsheet and the backsheet, and a fluid distribution material in between the topsheet and the absorbent core. The fluid distribution material includes a formed film according to embodiments of the invention described herein.

In an embodiment, the topsheet is directly bonded to the fluid distribution material. In an embodiment, the topsheet is vacuum laminated to the fluid distribution material. In an embodiment, the topsheet includes a formed film. In an embodiment, the topsheet includes a film/nonwoven laminate.

These and other aspects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

FIG. 2A is a photograph of a top view (user facing side) of an embodiment of a formed film that may be used as a fluid distribution material of the absorbent article of FIG. 1;

FIG. 2B is a photograph of a top perspective view of the formed film of FIG. 2A;

FIG. 2C is a schematic cross-sectional view of the formed film of FIG. 2A taken along line 2C-2C of FIG. 2A;

FIG. 11A is a photograph of a top view of a laminate a topsheet/fluid acquisition layer according to an embodiment of the invention; and FIG. 11B is an enlarged photograph of a cross-section of the laminate of FIG. 11A taken along lines 11B-11B.

DETAILED DESCRIPTION

Figure 1:
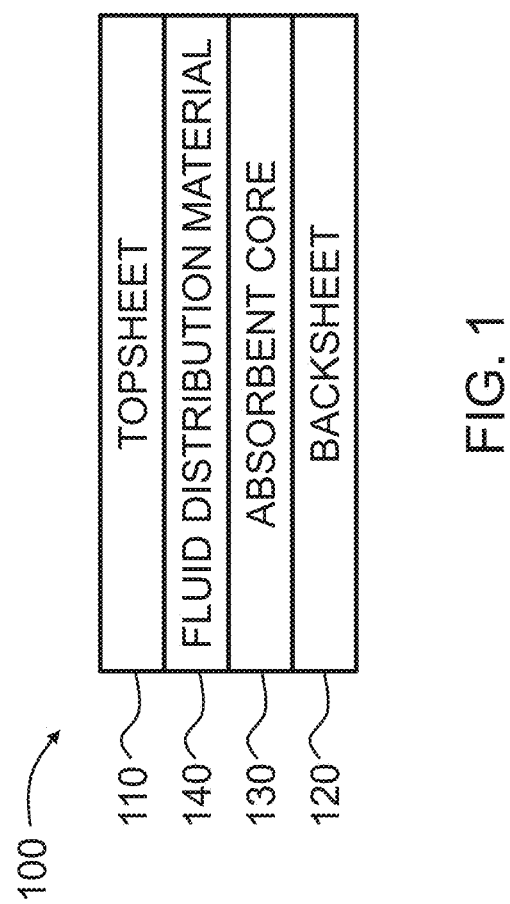
FIG. 1 is a schematic representation of an absorbent article in accordance with embodiments of the invention.

As used herein, the expression "absorbent articles" denote articles that absorb and contain body fluids and other body exudates. More specifically, an absorbent article/absorptive device includes garments that are placed against or in proximity to the body of a wearer to absorb and contain the various exudates discharged from a body. Non-limiting examples of absorbent articles include, but are not limited to feminine hygiene products, baby diapers, adult incontinence products, and bandages.

Throughout this description, the term "web" refers to a material capable of being wound into a roll. Webs can be film webs, nonwoven webs, laminate webs, apertured laminate webs, etc. The face of a web refers to one of its two dimensional surfaces, as opposed to one of its edges.

The term "film" or "polymer film" in this description refers to a web made by extruding a molten curtain or sheet of thermoplastic polymeric material by a cast or blown extrusion process and then cooling the sheet to form a solid polymeric web. Films can be monolayer films, coextruded films, coated films, and/or composite films.

Throughout this description, the expression "apertured films" denote films that have a plurality of apertures that extend from a first surface of the film to a second, opposing surface of the film.

A "two-dimensional apertured film" is a film in which no three-dimensional structure exists in the apertures, which then connect the second surface of a flat film to the first surface of the film.

A "formed film" or a "three-dimensional film" is a film with protuberances or protrusions extending from at least one side thereof, and an "apertured formed film" or a "three-dimensional apertured film" is a film in which a three-dimensional structure exists in the apertures (e.g., the apertures have a depth that is thicker than the thickness of the film), or the protuberances or protrusions or extended cells have apertures therethrough.

The term "protuberance" as used herein refers to a three-dimensional member comprising an apertured base portion located in the plane of the first surface of the film and a sidewall portion extending generally in the direction away from the first surface of the film. Each base portion has an associated sidewall portion. Sidewall portions terminate in "distal ends" located in the plane spaced from the first surface of the film. The distal ends of the protuberances may be apertured or unapertured.

"Apertured protuberance" as used herein refers to a protuberance that has an aperture at its base portion or proximal end in the plane of the first surface, as well as its distal or protubered end. The apertures in the base portions of the protuberances, also called "primary apertures," may be in the shape of polygons, for example squares, hexagons, pentagons, ellipses, circles, ovals, or slots, in a regulated or random pattern. In an embodiment, the apertures may be in the shape of a boat, as described in, for example, U.S. Pat. No. 7,198,836, which is incorporated herein by reference.

The apertured distal or protubered ends are called "secondary apertures," and may be in the shape of polygons, e.g., squares, hexagons, pentagons, ellipses, circles, ovals, slots, or boats. The sidewall portion of the apertured protuberance extends from the primary aperture to the secondary aperture.

The term "forming structure" or "screen" as used herein refers to a three-dimensional molding apparatus that comprises indentations and/or raised portions or protrusions used to form protuberances, and/or apertures in films. In an embodiment, forming structures comprise tubular members, having a width and a diameter. In alternative embodiments, forming structures may comprise belts having a width and a length. The transverse direction is the direction parallel to the width of the forming structure. The machine direction is the direction parallel to the direction of rotation of the forming structure, and is perpendicular to the transverse direction.

Various embodiments of the present invention will now be described. The discussion of any one embodiment is not intended to limit the scope of the present invention. To the contrary, aspects of the embodiments are intended to emphasize the breadth of the invention, whether encompassed by the claims or not. Furthermore, any and all variations of the embodiments, now known or developed in the future, also are intended to fall within the scope of the invention.

FIG. 1 schematically illustrates an absorbent article 100 in accordance with embodiments of the invention. As illustrated, the absorbent article 100 includes a topsheet 110, a backsheet 120, and an absorbent core 130 positioned in between the topsheet 110 and the backsheet 120. The absorbent article 100 also includes a fluid distribution material 140 positioned in between the topsheet 110 and the absorbent core 130.

The topsheet 110, which may be in the form of a two-dimensional or three-dimensional apertured film, a nonwoven web, or a laminate of an apertured film and a nonwoven web, is permeable to fluids and is configured to face the user wearing the absorbent article 100 and contact the user's skin. The topsheet 110 may be bonded directly to the fluid distribution material 140 by any known means in the art, including by not limited to adhesive bonding, thermal bonding, thermal point bonding, sonic bonding, and vacuum formed lamination (as described below), prior to assembly of the absorbent article 100.

The topsheet 110 receives insults of fluid from the user, and the fluid passes through the topsheet 110 to the fluid distribution material 140. The fluid distribution material 140 is also permeable and is configured to receive the fluid from the topsheet 110 and distribute the fluid to the absorbent core 130. The absorbent core 130, which includes absorbent materials, receives the fluid from the fluid distribution material 140 and stores the fluid until the absorbent article 100 is discarded. The backsheet 120, which is impermeable to liquid and may be in the form of a polymer film or laminate of a polymer film and nonwoven web, prevents liquid and other body exudates from leaking out of the bottom side of the absorbent core 130. The backsheet 120 may be breathable so that air, but not liquid, may pass through.

Figure 2D:
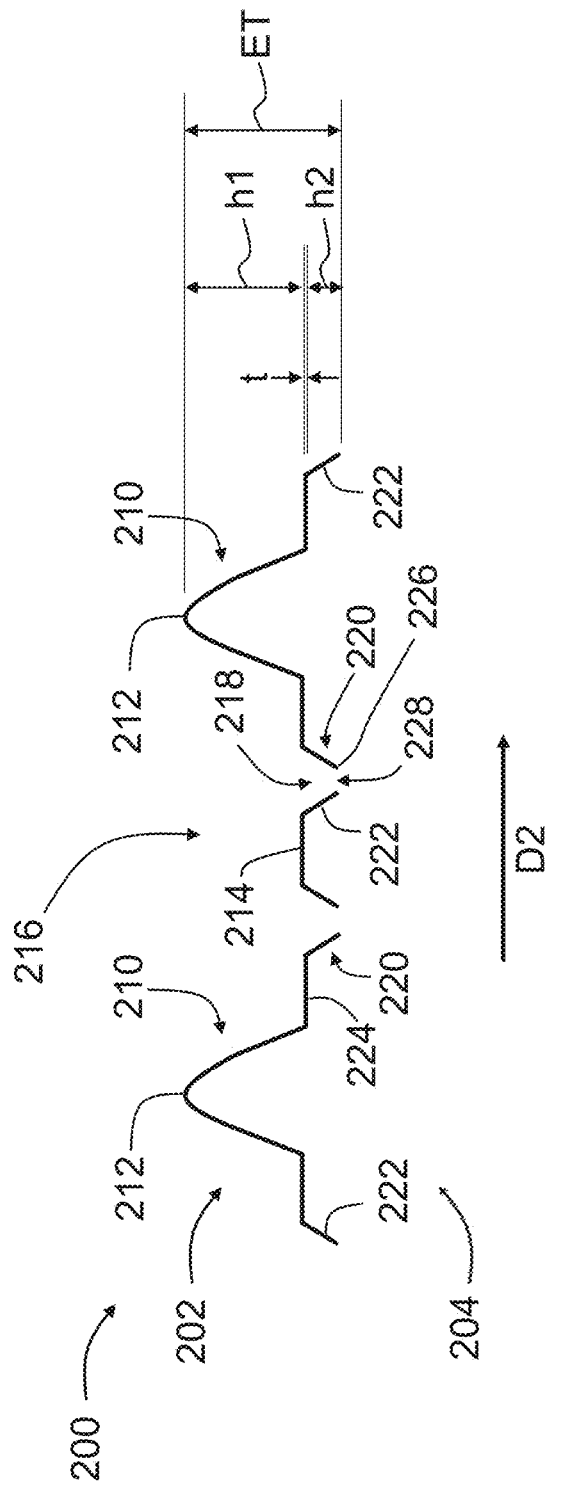
FIG. 2D is an enlarged schematic cross-sectional view of 2D in FIG. 2C.

FIG. 2A is a photograph of a top portion of a formed film 200 (user facing side) according to an embodiment of the invention, which may be used as the fluid distribution material 140 of FIG. 1, and FIG. 2B is a top perspective view of the formed film of FIG. 2A. FIG. 2C is a schematic cross-sectional view of the formed film 200 taken along line 2C-2C in FIG. 2A, and FIG. 2D is an enlarged view of a portion of the film circled as 2D in FIG. 2C. As illustrated, the formed film 200 includes a first side 202, which in an embodiment is configured to face the topsheet 110 of the absorbent article 100, and a second side 204, which in an embodiment is configured to face the absorbent core 130 of the absorbent article 100. In an embodiment, the first side 202 of the formed film 200 may be oriented to face the absorbent core 130, and the second side 204 of the formed film 200 may be oriented to face the topsheet 110.

The first side 202 includes a plurality of protrusions in the form of elongated ridges 210 that are oriented in a first direction D1 of the formed film 200 and have peaks 212 that are spaced from a first land area 214 of the first side 202 by a distance h1. The first side 202 also includes a plurality of valleys 216 defined by adjacent elongated ridges 210 and the first land area 214. The valleys 216 alternate with the elongated ridges 210 in a second direction D2, orthogonal to the first direction D1, and are oriented in the first direction D1. The first side 202 also includes a plurality of primary apertures 218 located at bottoms of the valleys 216.

The second side 204 of the formed film 200 includes a plurality of apertured protuberances 220. Each apertured protuberance 220 has a continuous side wall 222 that extends away from a second land area 224 to a distal end 226. The distal end 226 has a secondary aperture 228 that is substantially aligned with a corresponding primary aperture 218 of the first side 202. The distal ends 226 are spaced from the second land area 224 by a distance h2. The thickness ET of the formed film 200 is the sum of the nominal thickness of the film t between the first and second land areas 214, 224, and the height h1 of the elongated ridges 210, and the height h2 of the apertured protuberances 220.

In an embodiment, the apertured protuberances 220 may be arranged in a pattern having about 5 to about 45 protuberances per linear inch or "mesh," i.e., about 5 mesh to about 45 mesh in at least one direction. The pattern may be a hexagonal pattern, a square pattern, a staggered pattern, or any other type of pattern or design.

The polymer of the formed film 200 may include one or more polyolefins, including but not limited to polyethylene, ultra-low density polyethylene, low density polyethylene, linear low density polyethylene, linear medium density polyethylene, high density polyethylene, polypropylene, ethylene-vinyl acetates, metallocene, as well as other polymers, such as bio-based polymers that are produced from plants, including but not limited to sugarcane, or polylactic acid ("PLA"). Other polymers include, but are not limited to, elastomeric polymers, including but not limited to polypropylene based elastomers, ethylene based elastomers, copolyester based elastomers, olefin block copolymers, styrenic block copolymers and the like, or combinations thereof. Additives, such as surfactants, fillers, colorants, opacifying agents and/or other additives known in the art may also be used in the formed film 200.

In an embodiment, the formed film 200 has a basis weight between about 14 gsm and about 40 gsm. In an embodiment, the formed film has a basis weight between about 20 and about 35 gsm.

Figure 3:
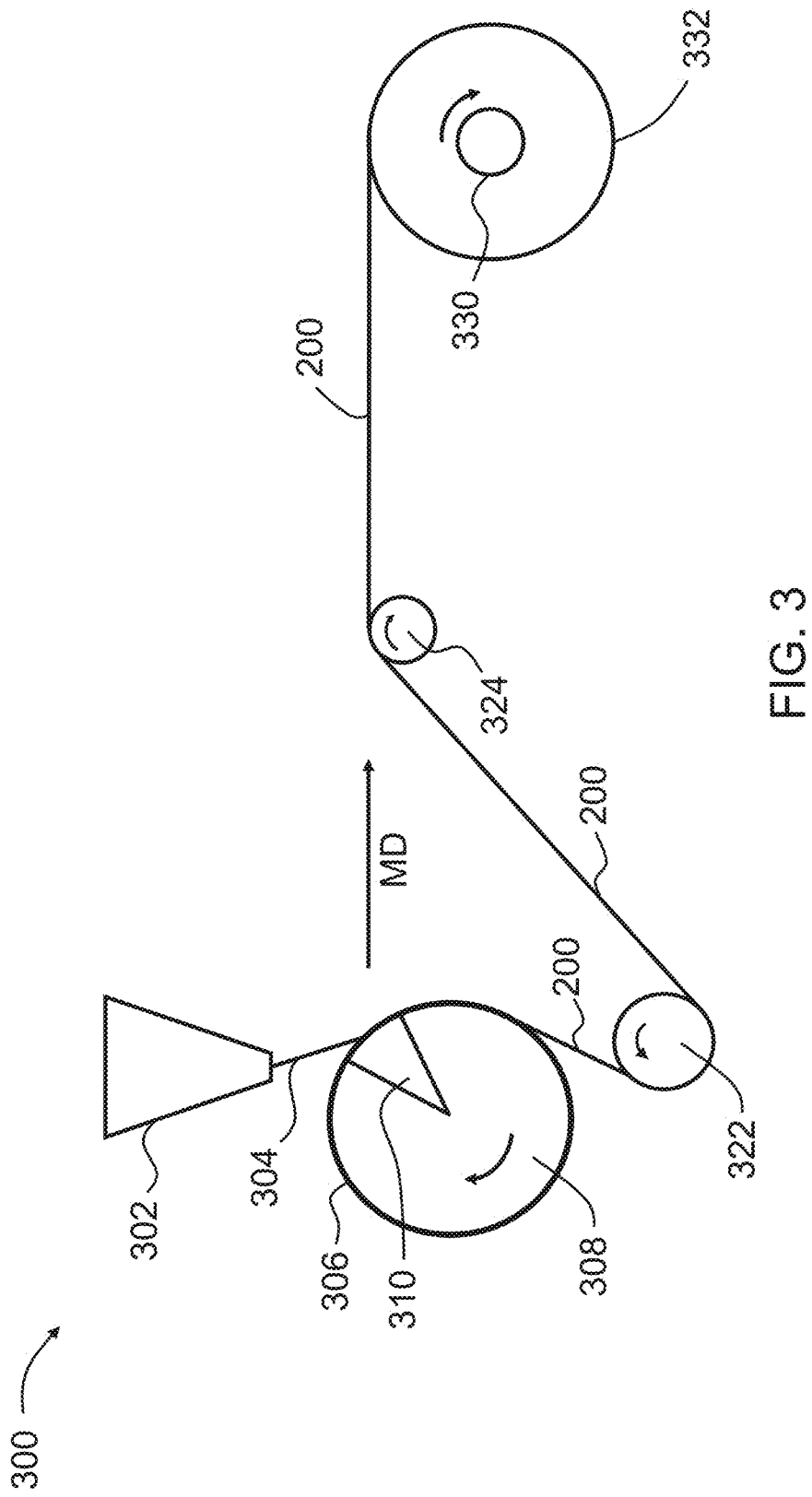
FIG. 3 is a schematic representation of an apparatus for manufacturing the film of FIGS. 2A-2D in accordance with embodiments of the invention.

FIG. 3 schematically illustrates an apparatus 300 that may be used to manufacture the formed film 200 of embodiments of the invention described herein. As illustrated, an extrusion die 302 extrudes a polymer melt curtain 304 onto a forming structure 306 that rotates about a cylinder 308 that has a vacuum slot 310 through which a vacuum is pulled. The forming structure 306 includes a plurality of apertures and a plurality of protrusions extending from an outer surface thereof. The polymer melt curtain 304 may include, for example, one or more polyolefin materials and a surfactant, as well as one or more additives, such as a colorant.

As the polymer web (which solidifies to form, for example, the formed film 200 of FIGS. 2A and 2B) is apertured, air flow is initiated through the apertured protuberances 220 which cools and solidifies the apertured protuberances 220. At the same time, the protrusions on the forming structure 306 shape the polymer web to form the elongated ridges 210. In an embodiment, the protrusions on the forming structure 306 that formed the elongated ridges 210 may be oriented in a machine direction MD. In an embodiment, the protrusions on the forming structure 306 that formed the elongated ridges 210 may be oriented in a cross direction orthogonal to the machine direction MD. The polymer web is also cooled by the forming structure 306. The resulting vacuum formed film 200 is pulled off of forming structure 306 by a peel roller 322 and travels to one or more subsequent rollers 324 until it may be wound by a winder 330 into a roll 332. Additional rollers and/or other pieces of equipment may be used in the apparatus 300. The illustrated embodiment is not intended to be limiting in any way.

EXAMPLES

Comparative: A secondary topsheet ("STS") material, which was positioned between the topsheet and absorbent core and in the form of a spunlace nonwoven material having a basis weight of 50 grams per square meter (gsm), was removed from an ALWAYS® Ultra Thin Feminine Hygiene Pad (Size 2) manufactured by The Procter & Gamble Company of Cincinnati, Ohio and used as a prior art Comparative Example ("Comparative STS").

Example 1: A formed film 200 having the structure illustrated in FIGS. 2A-2D and basis weight of 34 grams per square meter (gsm) was made on the apparatus 300 of FIG. 3 and used as Example 1.

Example 2: A formed film 200 having the structure illustrated in FIGS. 2A-2D and basis weight of 26 grams per square meter (gsm) was made on the apparatus 300 of FIG. 3 and used as Example 2.

Figure 4:
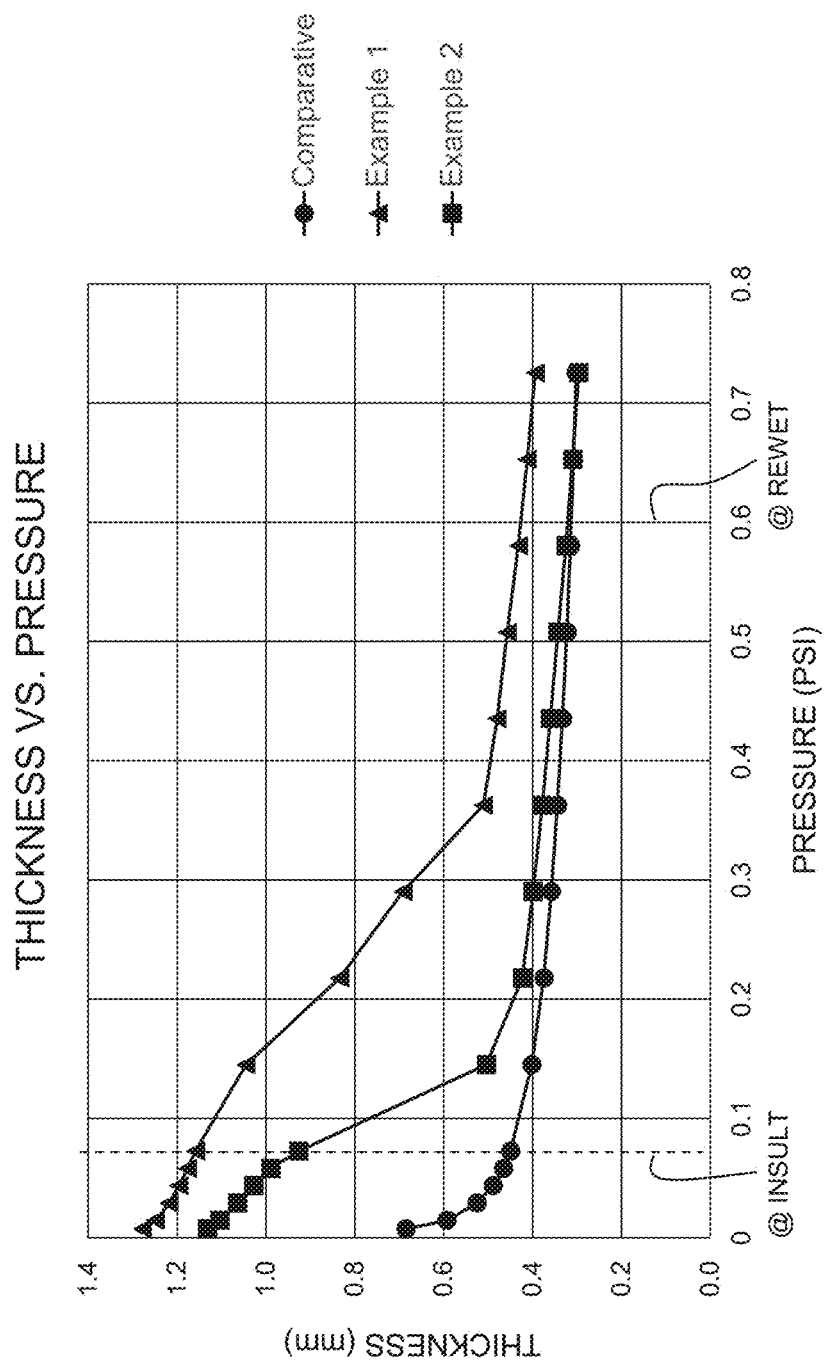
FIG. 4 is a plot illustrating thicknesses of the formed film according to embodiments of the invention, as well as a prior art comparative fluid distribution material as a function of applied pressure.

The materials of the Comparative STS, Example 1 and Example 2 were measured for thickness (compression resistance) under pressures ranging from 0.00725 psi to 0.725 psi using a VantageNx universal testing machine with a compression fixture by Thwing-Albert Instrument Company. The opening distance between two plates within the instrument was set to 1.27 cm (0.5 inch). Each sample was placed on a lower plate in the instrument and an upper plate was manually lowered to a position just above, but not touching, the sample before the test was started. Three samples for each material were measured and the results were averaged. The results of the testing are illustrated in FIG. 4. The Comparative STS had a lower initial thickness, and all three examples had their thicknesses decrease as the applied pressure was increased, as expected. Example 2 exhibited similar thicknesses as the Comparative STS at pressures above 0.2 psi, and Example 1 exhibited greater thicknesses at all pressures.

In order to test performance of the formed film 200 when used as a fluid distribution material 140 in an absorbent article 100, specifically in a feminine hygiene pad, the STS materials of several ALWAYS® Ultra Thin Feminine Hygiene Pads (size 2) manufactured by The Procter & Gamble Company of Cincinnati, Ohio were removed and replaced with the formed films of Examples 1 and 2 with the distal ends 226 of the apertured protuberances 220 contacting the absorbent core and the peaks 212 of the plurality of elongated ridges 210 contacting the topsheet. The first direction D1 of the formed film 200 was oriented parallel to the length (longer dimension) of the pad so that the plurality of elongated ridges 210 were oriented parallel to the length of the pad. In addition, Comparative Example A was the as-manufactured ALWAYS® Ultra Thin Feminine Hygiene Pad (size 2), and Comparative Example B was the as-manufactured ALWAYS® Ultra Thin Feminine Hygiene Pad (size 2) after the STS material was removed and placed back into the pad in the same manner that was done with Examples 1 and 2.

Examples 1 and 2, and Comparative Examples A and B, described above, were tested for performance characteristics, including multiple strikethrough times and rewet values. For each example, three pads were subjected to three insults of 4 milliliters (ml) of a synthetic blood having a viscosity of 11.1 centipoise (cP), and rewet values were measured after each insult. Specifically, each pad was placed on a flat table top, a 500 g strikethrough plate made from clear plastic with a hole in the center, which resulted in an applied pressure of about 0.071 psi, was placed on top of the topsheet of each pad so that the hole in the plate was centered on the topsheet, and a pump was started to deliver the 4 ml insult in 6 seconds. A stopwatch was started at the same time the pump was started and stopped when the insult liquid in the plate hole was observed to be absorbed by the pad. The recorded time was the first insult strikethrough time in seconds.

The strikethrough plate was removed, five sheets of pre-weighed pickup paper were placed over the insult area and a 4.8 lb. weight, which resulted an applied pressure of 0.6 psi, was placed on top of the sheets of paper for two minutes. After the two minutes, the weight and the five sheets of paper were removed, a picture was taken of the pad, and the five sheets of papers were weighed. The difference between the weight of the "wet" paper and the initial "dry" paper was the measured rewet value in grams. The procedure was repeated for a second insult and a third insult on the same pad.

Figure 5A:
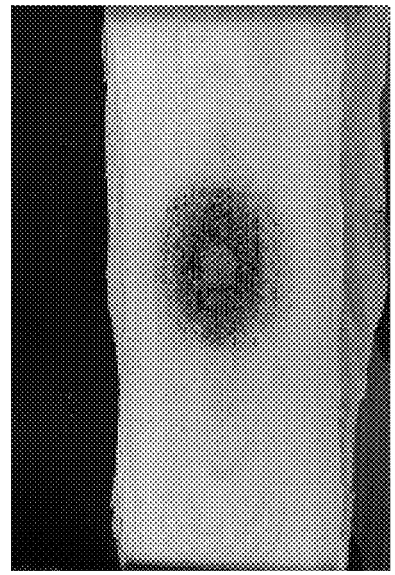
FIG. 5A is a photograph of a prior art absorbent article after a first insult of synthetic blood.
Figure 5B:
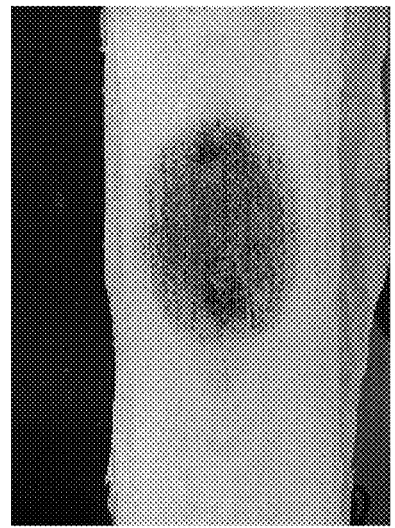
FIG. 5B is a photograph of the prior art absorbent article of FIG. 5A after a second insult of synthetic blood.
Figure 5C:
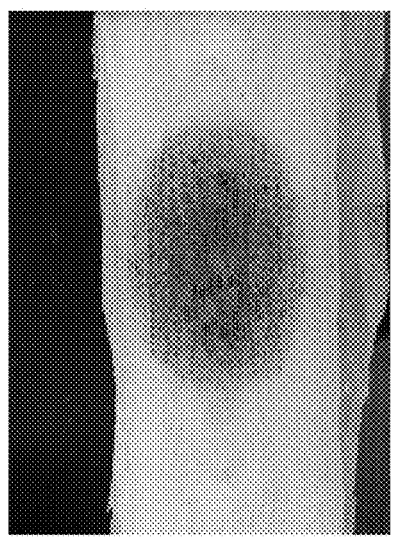
FIG. 5C is a photograph of the prior art absorbent article of FIG. 5B after a third insult of synthetic blood.
Figure 6A:
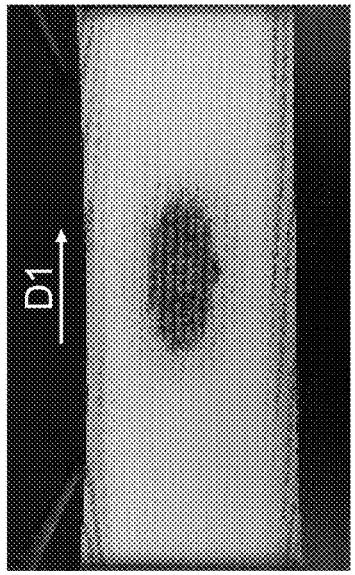
FIG. 6A is a photograph of an absorbent article with a formed film used as a fluid distribution material according to an embodiment of the invention after a first insult of synthetic blood.
Figure 6B:
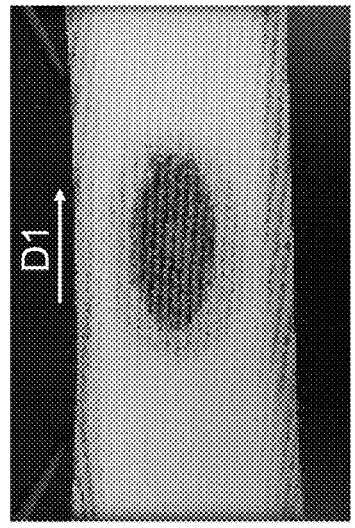
FIG. 6B is a photograph of the absorbent article of FIG. 6A after a second insult of synthetic blood.
Figure 6C:
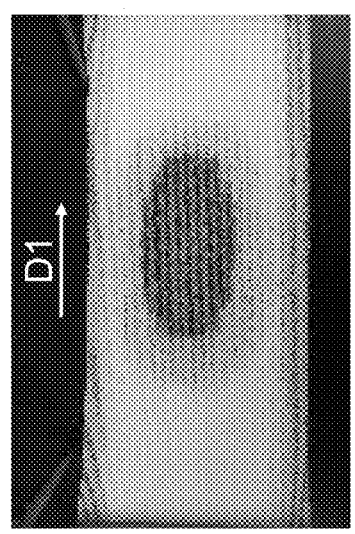
FIG. 6C is a photograph of the absorbent article of FIG. 6B after a third insult of synthetic blood.

FIGS. 5A-5C illustrate the Comparative Example A pads after the first, second, and third insults, respectively, while FIGS. 6A-C illustrate the Example 1 pads after the first, second, and third insults, respectively. As illustrated, the Example 1 pads had stains that were more elongated than the stains of the Comparative Example A stains, which indicates that the structure provided by the formed film 200 helped direct the insult along the length of the pad. Such direction flow may help prevent undesirable side leakages that may be experienced by the user.

Figure 7:
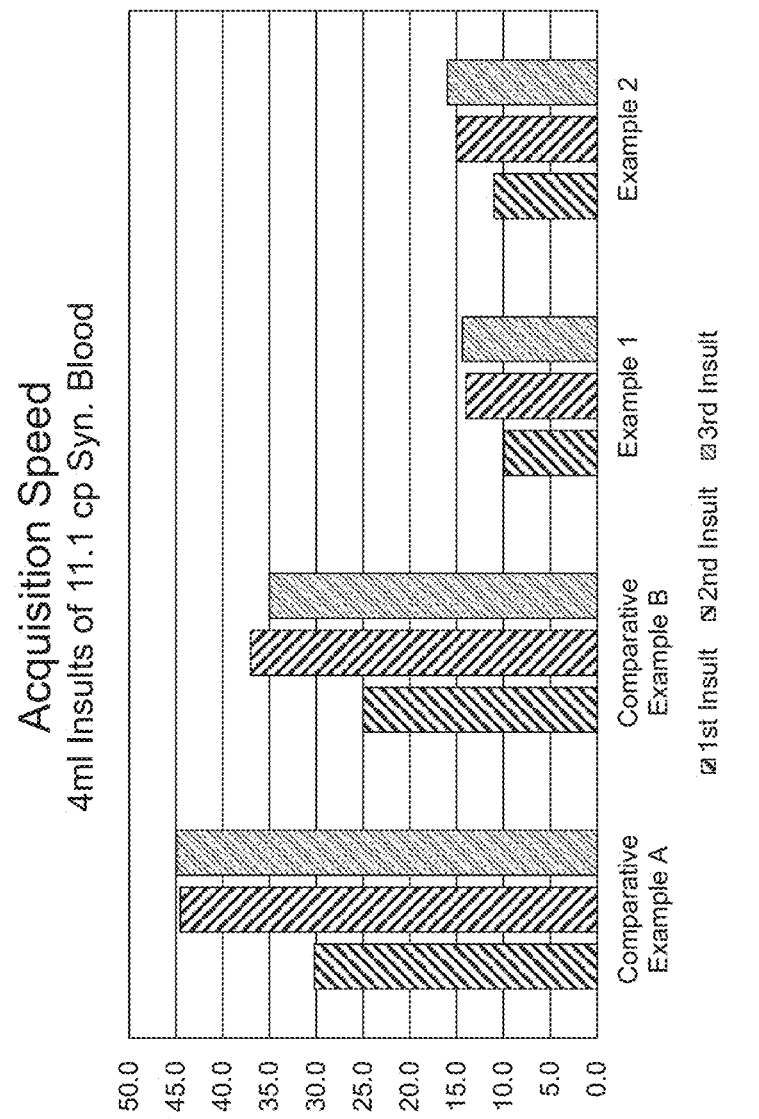
FIG. 7 is a plot of acquisition speeds of each of three insults of synthetic blood for prior art absorbent articles and absorbent articles with formed films used as fluid distribution materials according to embodiments of the invention.
Figure 8:
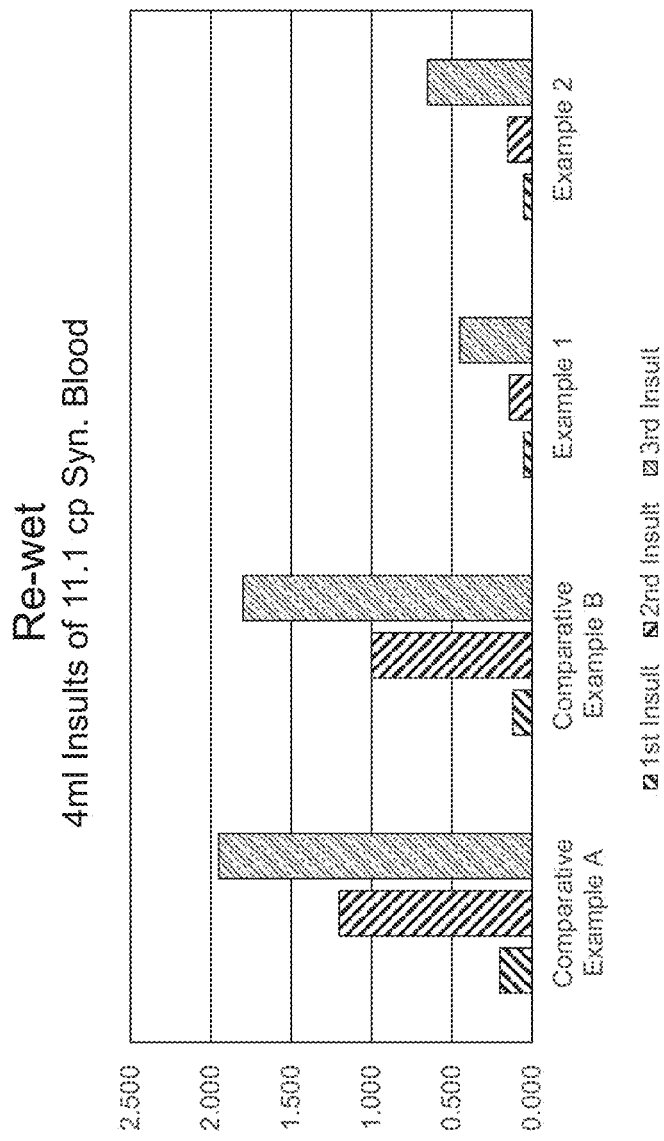
FIG. 8 is a plot of rewet values after each of three insults of synthetic blood for the prior art absorbent articles and absorbent articles with formed films used as fluid distribution materials according to embodiments of the invention.

The results of the strikethrough and rewet tests (averages of three specimens each) are illustrated in FIGS. 7 and 8. Specifically, FIG. 7 is a plot of acquisition speeds of each of the three insults of synthetic blood for the Comparative Example A, Comparative Example B, Example 1, and Example 2 pads, and FIG. 8 is a plot of rewet values after each of the three insults of synthetic blood for the same pads. Both Example 1 and Example 2 exhibited faster acquisition speeds and lower rewet values after each insult, as compared to Comparative Example A and Comparative Example B, thereby indicating improvements in removing the fluid from the topsheet and delivering the fluid to the absorbent core, as well as preventing the fluid from returning to the top of the topsheet, even while under pressure.

Returning to FIG. 4, it is noted that the thicknesses of the Example 1 and Example 2 formed films at the pressure corresponding to the insult pressure (about 0.071 psi) are significantly higher than the thickness of the Comparative STS, which provides more void volume beneath the topsheet and allows the fluid to pass through the topsheet more quickly. The thicknesses of the Example 2 formed film and the Comparative STS are about the same at the rewet pressure (about 0.6 psi), while the thickness of the Example 1 formed film is slightly higher than the thickness of the Comparative STS, yet the Example 1 and Example 2 pads exhibited much better (lower) rewet values. Not to be bound by theory, it is postulated that the reason Example 2 performed better than the Comparative STS is due to more extensive use of the absorbent core 130, or spreading, leading to additional material being bound in the absorbent core 130.

Figure 9:
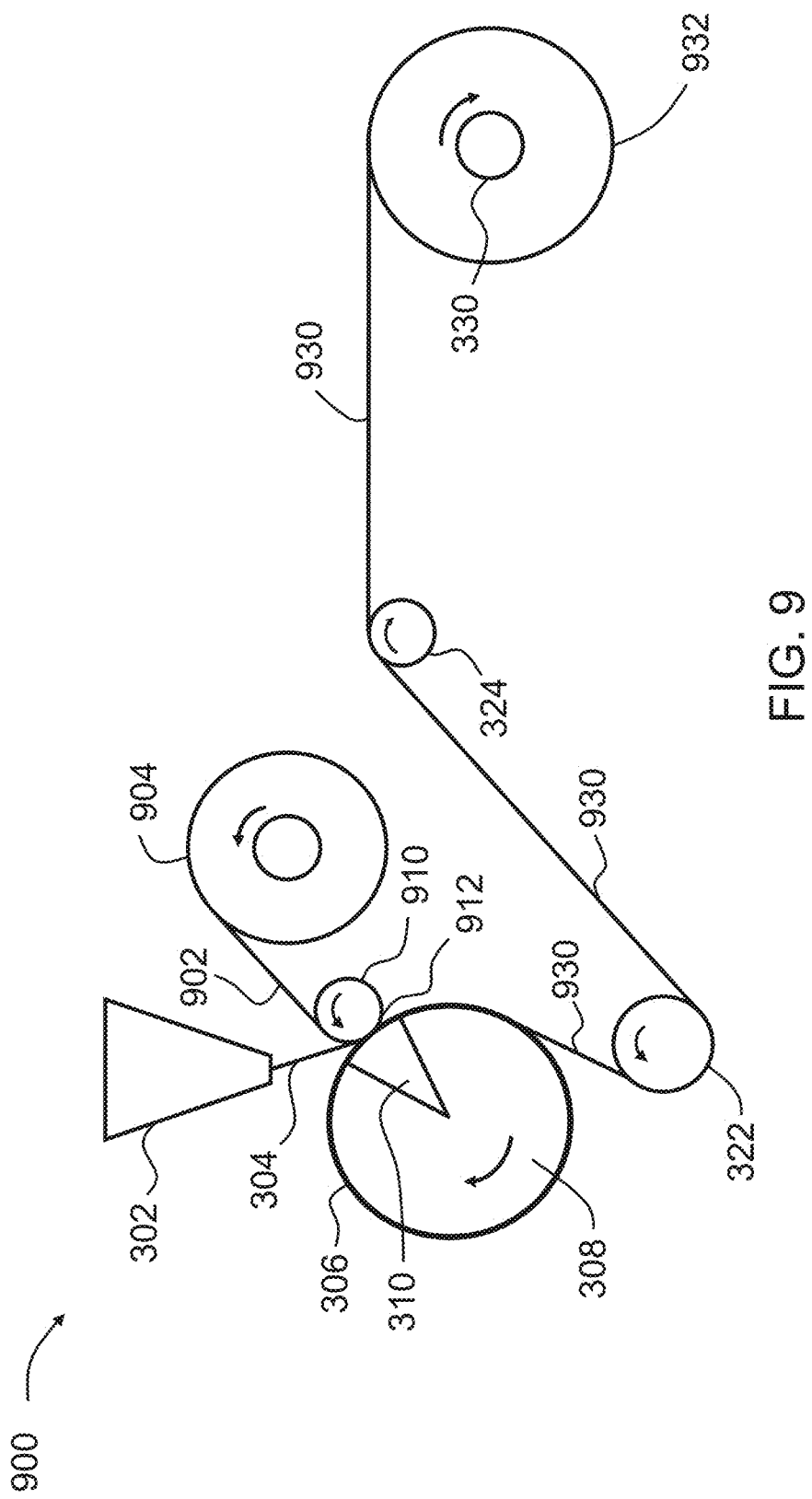
FIG. 9 is a schematic representation of an apparatus for manufacturing a laminate in accordance with embodiments of the invention.

In an embodiment, the formed film 200 may be laminated to a topsheet material so that the topsheet 110 and fluid distribution material 140 are bonded together before being assembled in the absorbent article 100, as discussed above. To this end, FIG. 9 schematically illustrates an apparatus 900 that may be used to manufacture a vacuum laminate of the topsheet 110 and the fluid distribution material 140, with the fluid distribution material being the formed film 200 described above. As illustrated, the extrusion die 302 extrudes the polymer melt curtain 304 onto the forming structure 306 as a topsheet material 902 that has been previously formed is unwound from a roll 904 using a laminating roller 910. The melt curtain 304 is still molten at an impingement point 912 between the forming structure 306 and the laminating roller 910. This allows the melt curtain 304 to bond to the topsheet material 902 while the apertures and elongated ridges are created in the melt curtain 304 to create the formed film 200 described above. The resulting topsheet/fluid distribution material laminate 930 may be wound by the winder 330 into a roll 932. The topsheet material 902 may be a formed film, a nonwoven, a film/nonwoven laminate, a film/film laminate, etc.

Figure 10B:
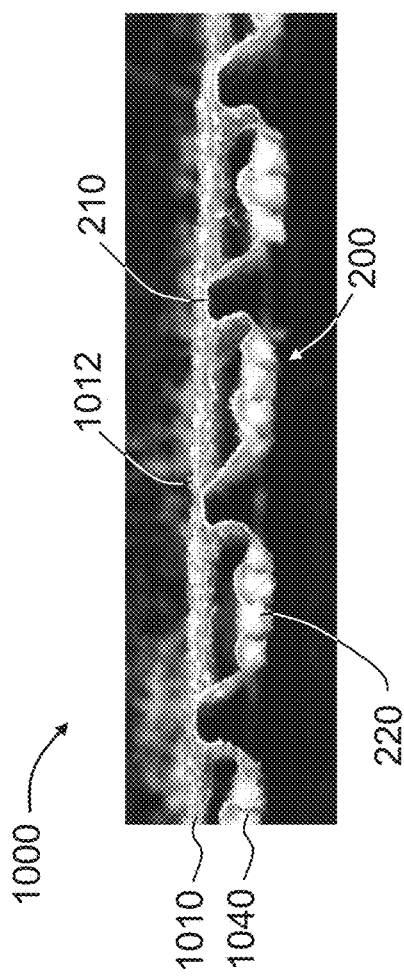
FIG. 10B is an enlarged photograph of a cross-section of the laminate of FIG. 10A taken along lines 10B-10B.
Figure 10A:
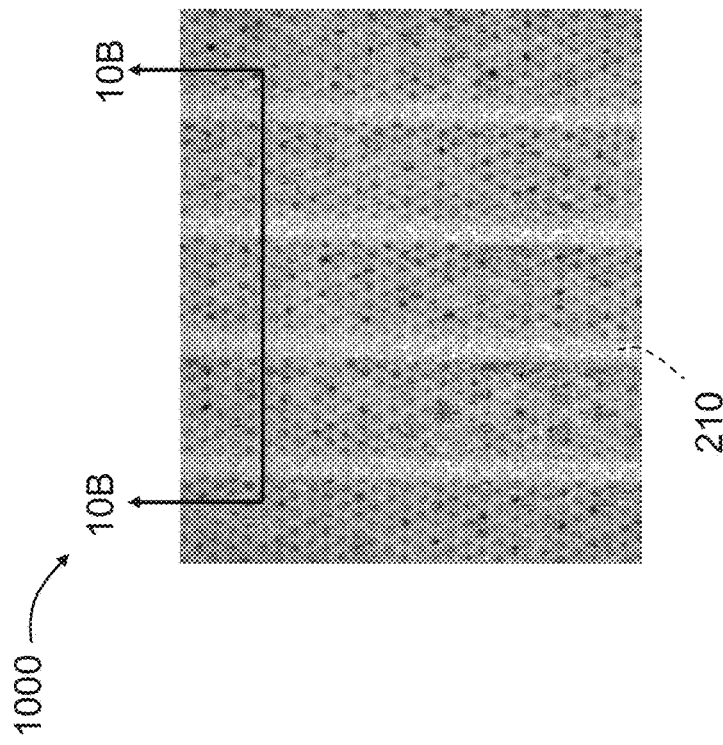
FIG. 10A is a photograph of a top view of a laminate of a topsheet/fluid acquisition layer according to an embodiment of the invention.

FIG. 10A is a photograph of a top view of a laminate 1000 of a topsheet 1010 and a fluid acquisition layer 1040 according to an embodiment of the invention, and FIG. 10B is an enlarged photograph of a cross-section of the laminate 1000 of FIG. 10A taken along lines 10B-10B. In this embodiment, the topsheet 1010 is a film/nonwoven laminate with a film layer having a plurality of apertured protuberances 1012 having a mesh count of about 60 apertured protuberances per linear inch extending away from a nonwoven layer. The fluid acquisition layer 1040 is the formed film 200 described above. Fibers of the nonwoven layer of the topsheet 1010 are embedded in the ridges 210 of the formed film 200/fluid acquisition layer 1040.

FIG. 11A is a photograph of a top view of a laminate 1100 of a topsheet 1110 and fluid acquisition layer 1140 according to an embodiment of the invention, and FIG. 11B is an enlarged photograph of a cross-section of the laminate 1100 of FIG. 11A taken along lines 11B-11B. In this embodiment, the topsheet 1110 is a formed film having a plurality of micro protuberances 1112, which may or may not be apertured, and a plurality of macro apertured protuberances 1114. The fluid acquisition layer 1140 is the formed film 200 described above. Portions of the topsheet 1110 are bonded to the ridges 210 of the formed film 200/fluid acquisition layer 1140.

The embodiments described herein represent a number of possible implementations and examples and are not intended to necessarily limit the present disclosure to any specific embodiments. Instead, various modifications can be made to these embodiments, and different combinations of various embodiments described herein may be used as part of the invention, even if not expressly described, as would be understood by one of ordinary skill in the art. Any such modifications are intended to be included within the spirit and scope of the present disclosure and protected by the following claims.

What is claimed is:

1. A formed film for use as a fluid distribution material in an absorbent article comprising a topsheet, a backsheet, and an absorbent core between the topsheet and backsheet, the formed film being positionable between the top sheet and the absorbent core, the formed film comprising:
   a first side comprising
      a plurality of protrusions in the form of elongated ridges having peaks extending from a first land area of the first side and oriented in a first direction,
      a plurality of valleys defined by adjacent protrusions and the first land area and oriented in the first direction, and
      a plurality of primary apertures located at bottoms of the valleys; and
   a second side opposite the first side, the second side comprising
      a plurality of apertured protuberances, each of the apertured protuberances comprising a continuous sidewall extending from a second land area of the second side to a distal end comprising a secondary aperture, wherein each secondary aperture is substantially aligned with a primary aperture,
   wherein the formed film has a thickness greater than about 0.9 mm under a pressure of 0.071 psi, and a thickness greater than about 0.3 mm under a pressure of 0.6 psi,
   wherein the plurality of protrusions excludes the plurality of primary apertures and the plurality of apertured protuberances,
   wherein the plurality of protrusions are narrower than the plurality of valleys, and
   wherein the peaks are spaced from the first land area by a first distance that is uniform from a first end to a second end in the first direction.

2. The formed film according to claim 1, wherein the first side is configured to face the topsheet and the second side is configured to face the absorbent core.

3. The formed film according to claim 1, wherein the formed film has a basis weight between about 14 gsm and about 40 gsm.

4. The formed film according to claim 1, wherein the plurality of apertured protuberances are arranged in a pattern having about 5 to about 45 apertured protuberances per linear inch in the first direction.

5. The formed film according to claim 1, wherein the plurality of apertured protuberances are spaced from the second land area by a second distance.

6. The formed film according to claim 1, wherein the first distance is greater than the second distance.

7. The formed film according to claim 1, wherein the primary apertures comprise more than one primary aperture between adjacent peaks in a second direction orthogonal to the first direction.

8. An absorbent article comprising:
   a topsheet configured to contact skin of a user of the absorbent article;
   a backsheet configured to contact a garment of the user of the absorbent article;
   an absorbent core in between the topsheet and the backsheet; and
   a fluid distribution material in between the topsheet and the absorbent core, the fluid distribution material comprising a formed film of claim 1.

9. The absorbent article according to claim 8, wherein the topsheet is directly bonded to the fluid distribution material.

10. The absorbent article according to claim 9, wherein the topsheet is vacuum laminated to the fluid distribution material.

11. The absorbent article according to claim 9, wherein the topsheet comprises a formed film.

12. The absorbent article according to claim 9, wherein the topsheet comprises a film/nonwoven laminate.

* * * * *